(12) United States Patent
Jasperse et al.

(10) Patent No.: US 9,606,067 B2
(45) Date of Patent: Mar. 28, 2017

(54) BIOLOGICAL ASSAY SAMPLE ANALYZER

(71) Applicant: Siemens Healthcare Diagnostics Inc., Tarrytown, NY (US)

(72) Inventors: Jeffrey R. Jasperse, West Newton, MA (US); Normand P. Desmarais, Cumberland, RI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/396,123

(22) PCT Filed: Apr. 23, 2013

(86) PCT No.: PCT/US2013/037712
§ 371 (c)(1),
(2) Date: Oct. 22, 2014

(87) PCT Pub. No.: WO2013/163129
PCT Pub. Date: Oct. 31, 2013

(65) Prior Publication Data
US 2015/0118690 A1    Apr. 30, 2015

Related U.S. Application Data

(60) Provisional application No. 61/636,860, filed on Apr. 23, 2012.

(51) Int. Cl.
*G01N 21/76* (2006.01)
*G01N 21/64* (2006.01)

(52) U.S. Cl.
CPC .......... *G01N 21/76* (2013.01); *G01N 21/645* (2013.01); *G01N 2021/6463* (2013.01);
(Continued)

(58) Field of Classification Search
CPC .... G01J 3/4406; G02B 21/086; G02B 21/088
See application file for complete search history.

(56) References Cited

U.S. PATENT DOCUMENTS

| 4,153,369 A | 5/1979 | Kallet et al. |
| 4,515,445 A * | 5/1985 | Muller ................ G02B 21/088 359/386 |

(Continued)

FOREIGN PATENT DOCUMENTS

| CN | 1549921 A | 11/2004 |
| CN | 1717579 A | 1/2006 |

(Continued)

OTHER PUBLICATIONS

International Search Report and Written Opinion of International Application No. PCT/US2013/037712 dated Sep. 13, 2013.

(Continued)

*Primary Examiner* — Nicole Ippolito
*Assistant Examiner* — Sean Luck
(74) *Attorney, Agent, or Firm* — Kyle D. Petaja

(57) ABSTRACT

A sample analyzer has an illuminator for illuminating an assay sample to cause luminescence, and a support for a sample vessel containing the assay sample. The support is adapted to position the assay sample proximate the illuminator. A detector is positioned along an optical axis extending from the illuminator, through the positioned assay sample, to the detector, so as to detect the luminescence from the assay sample. A reflector is removably disposed between the illuminator and the assay sample so as to reflect a portion of the luminescence back through the positioned assay sample toward the detector.

22 Claims, 8 Drawing Sheets

(52) U.S. Cl.
CPC .............. *G01N 2021/6471* (2013.01); *G01N 2021/6476* (2013.01); *G01N 2201/0245* (2013.01); *G01N 2201/0634* (2013.01); *G01N 2201/0636* (2013.01); *G01N 2201/0666* (2013.01)

(56) References Cited

U.S. PATENT DOCUMENTS

| | | | |
|---|---|---|---|
| 4,562,356 A | 12/1985 | Auth | |
| 4,795,256 A | 1/1989 | Krause et al. | |
| 5,575,977 A | 11/1996 | McKinney et al. | |
| 5,709,994 A | 1/1998 | Pease et al. | |
| 6,275,294 B1 | 8/2001 | Folestad | |
| 6,867,851 B2 | 3/2005 | Blumenfeld et al. | |
| 7,402,281 B2 | 7/2008 | Huynh-Ba et al. | |
| 2003/0044967 A1* | 3/2003 | Heffelfinger | G01J 3/14 435/287.2 |
| 2003/0137725 A1* | 7/2003 | Mueller | G02B 21/088 359/386 |
| 2004/0178370 A1* | 9/2004 | Oldham | G01J 3/10 250/559.4 |
| 2006/0188407 A1 | 8/2006 | Gable et al. | |
| 2008/0090198 A1* | 4/2008 | Liang | A61B 1/0638 433/29 |
| 2009/0153956 A1* | 6/2009 | Kusaka | G02B 21/08 359/385 |
| 2009/0218517 A1 | 9/2009 | Bedingham et al. | |
| 2009/0225407 A1* | 9/2009 | Nakayama | G02B 21/16 359/370 |
| 2010/0142038 A1* | 6/2010 | Sugiura | G02B 21/082 359/381 |
| 2011/0049385 A1* | 3/2011 | Laitinen | G01J 3/02 250/458.1 |
| 2011/0102888 A1* | 5/2011 | Honda | G02B 21/06 359/385 |
| 2011/0203924 A1 | 8/2011 | Wohlstadter et al. | |

FOREIGN PATENT DOCUMENTS

| | | |
|---|---|---|
| CN | 101189505 A | 5/2008 |
| CN | 101622522 A | 1/2010 |
| CN | 1302377 A | 7/2011 |
| EP | 0802413 A2 | 10/1997 |
| JP | S4989587 A | 8/1974 |
| JP | 2002277396 A | 9/2002 |
| JP | 2003207453 A | 7/2003 |
| JP | 2008537594 A | 9/2008 |
| JP | 2009128125 A | 6/2009 |
| WO | 2007133465 A2 | 11/2007 |

OTHER PUBLICATIONS

European Search Report and Search Opinion of European Application No. EP 13780950 dated Oct. 16, 2015.

Dafforn, Alan et al. "Miniaturization of the Luminescent Oxygen Channeling Immunoassay (LOCITM) for use in multiplex array formats and other biochips", Clinical Chemistry, vol. 46, No. 9, Sep. 2000, pp. 1495-1497, XP002745232.

Patel, Rajesh et al. "Quantification of DNA Using the Luminescent Oxygen Channeling Assay" Clinical Chemistry 46:9; pp. 1471-1477 (2000) / Jan. 9, 2000.

* cited by examiner

BIOLOGICAL ASSAY SAMPLE ANALYZER

CROSS-REFERENCE TO RELATED APPLICATIONS

The entirety of U.S. Provisional Application Ser. No. 61/636,860, filed on Apr. 23, 2012, is hereby expressly incorporated herein by reference.

STATEMENT REGARDING FEDERALLY SPONSORED RESEARCH OR DEVELOPMENT

Not applicable.

BACKGROUND OF THE INVENTIVE CONCEPTS

1. Field of the Inventive Concepts

The inventive concepts disclosed and claimed herein relate to a sample analyzer, and more particularly, but not by way of limitation, to sample analyzers having a reflector for improving photon collection efficiency from a luminescent assay sample.

2. Brief Description of Related Art

Chemiluminescence is the emission of light as the result of a chemical reaction. Various types of chemical analyses utilizing luminescence have been developed, and luminescent compounds, such as fluorescent compounds and chemiluminescent compounds, have been used as labels in assays such as nucleic acid assays and immunoassays. Various types of instrumentation utilizing luminescence measurements are heavily utilized in the pharmaceutical and medical industries. Analytical measurements are often performed using a beam of catalyzing radiation to interact with a specific sample-reagent combination. The resulting photon emission, often very weak, is then detected and measured with a sensitive detector, converted to an electrical signal, and further correlated to provide the actual analytical result.

For example, U.S. Pat. No. 5,709,994 discloses a highly sensitive method of assaying known as a Luminescent Oxygen Channeling Immunoassay (LOCI). The method uses a photosensitizer that generates singlet oxygen upon irradiation, and a chemiluminescent compound that is activated by the singlet oxygen. The photosensitizer and chemiluminescent compound are irradiated with light of a certain wavelength, after which the resulting light emitted by chemiluminescent compound is measured and correlated to provide the assay.

These analyses, or assays, typically involve automated analyzers into which vials containing patient samples have been loaded. Improved sample containers have been developed for high-throughput screening for new drug development. Continued improvements in methods and instrumentation have resulted in significantly increasing assay throughput and increasing speed.

The instrumentation utilized for luminescence-based assays is often physically large due, in part, to the intricate and sensitive optics used. Size is not a major concern in large laboratories facilitating high-throughput screening; however, it would be useful to have a lighter, portable unit or handheld device capable of producing accurate luminescence-based analyses. Especially in low light photon counting applications, designs that reduce power requirements, reduce the optical path necessary, and increase the photon collection efficiency, would help provide such a portable unit.

In view of the foregoing, there is a need for a luminescence-based sample analyzer having reduced sample size, reduced power requirements, reduced optical path, and increased photon collection efficiency. It is to such a luminescence sample analyzer that the presently disclosed and claimed inventive concept(s) is directed.

SUMMARY OF THE INVENTIVE CONCEPTS

The inventive concepts disclosed and claimed herein generally relate to a sample analyzer utilizing luminescence. The sample analyzer has an illuminator for illuminating an assay sample to cause luminescence, and a support for a sample vessel containing the assay sample. The support is adapted to position the assay sample proximate the illuminator. A detector for detecting the luminescence is positioned along an optical axis extending from the illuminator, through the positioned assay sample, to the detector. A reflector is removably disposed between the illuminator and the positioned assay sample, for reflecting a portion of the luminescence back through the positioned assay sample toward the detector.

In one embodiment, the reflector is disposed on a shuttle. The sample analyzer includes a shuttle controller configured to align the reflector with and perpendicular to the optical axis and adjacent the positioned sample during a measuring mode of analysis. The shuttle then moves the reflector away from the optical axis during an illumination mode.

In some embodiments, the detector is positioned between 3 to 15 mm from the positioned sample.

In another embodiment, the sample analyzer includes a light diffuser positioned between the illuminator and the shuttle. The light diffuser is aligned with and perpendicular to the optical axis and, in an illumination mode, diffuses light from the illuminator into the positioned sample. In yet another embodiment, the light diffuser is positioned on the shuttle.

A method of analyzing as assay sample includes the following steps. A sample analyzer is obtained, the sample analyzer comprising an illuminator, a support positioned to support a sample vessel containing an assay sample proximate the illuminator, a detector positioned along an optical axis extending from the illuminator, through the assay sample, to the detector, and a reflector removeably disposed between the illuminator and the assay sample. The sample vessel containing the assay sample is supported proximate the illuminator. The assay sample is illuminated to cause luminescence. The reflector is positioned between the illuminator and the assay sample to reflect a portion of the luminescence back through the assay sample toward the detector. The detector then measures the luminescence.

BRIEF DESCRIPTION OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, and drawings. The figures are not necessarily the scale and certain features and certain views of the figures may be shown exaggerated, to scale or in schematic in the interest of clarity and conciseness. In the drawings.

DETAILED DESCRIPTION OF EXEMPLARY EMBODIMENTS

Figure 1:
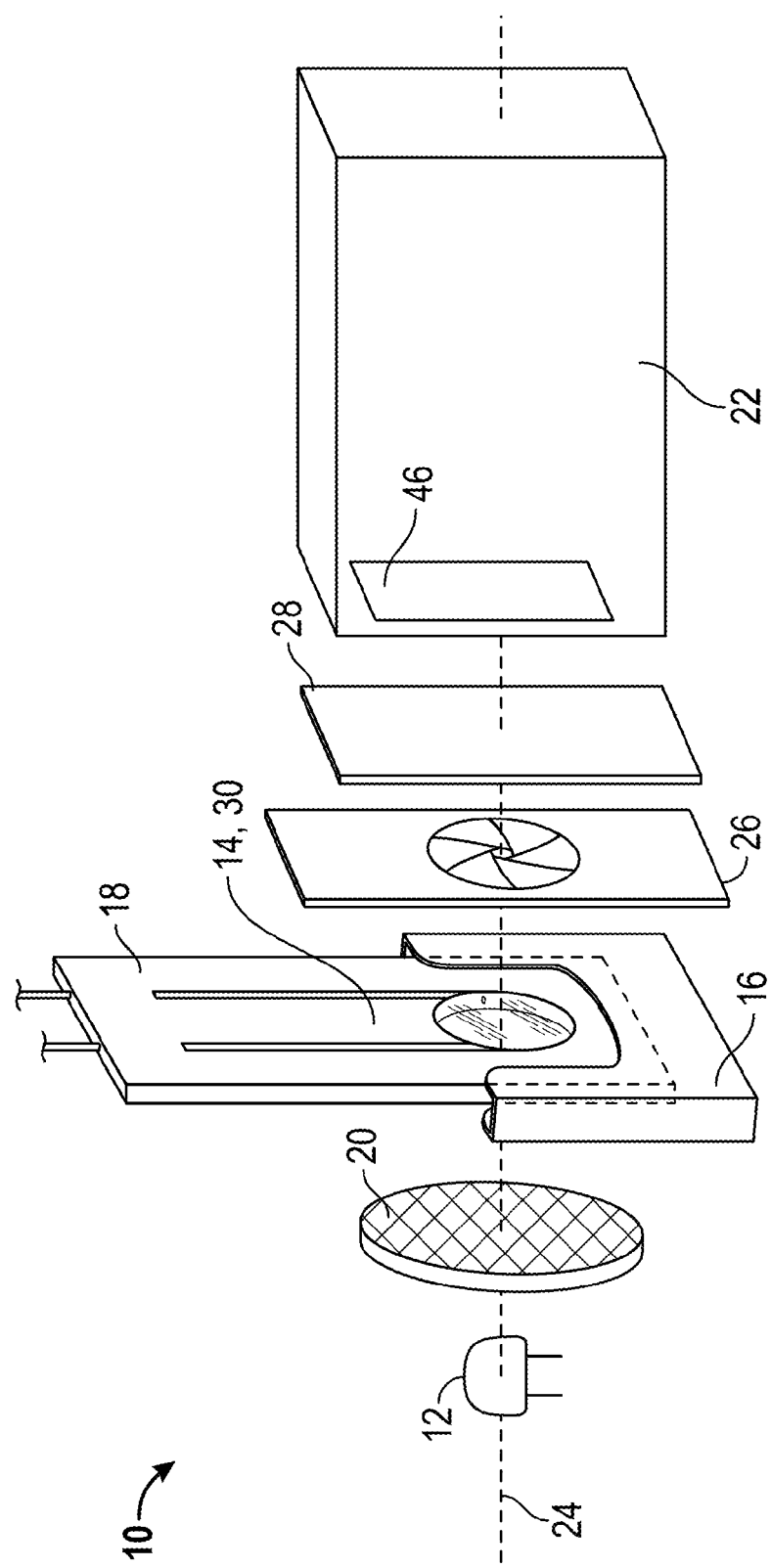
FIG. 1 is a schematic representation of an embodiment of a sample analyzer constructed in accordance with the inventive concepts disclosed herein.

Before explaining at least one embodiment of the inventive concept disclosed herein in detail, it is to be understood that the inventive concept is not limited in its application to the details of construction, experiments, exemplary data, and/or the arrangement of the components set forth in the following description, or illustrated in the drawings. The presently disclosed and claimed inventive concept is capable of other embodiments or of being practiced or carried out in various ways. Also, it is to be understood that the phraseology and terminology employed herein is for purpose of description only and should not be regarded as limiting in any way.

In the following detailed description of embodiments of the inventive concept, numerous specific details are set forth in order to provide a more thorough understanding of the inventive concept. However, it will be apparent to one of ordinary skill in the art that the inventive concept within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless it is obvious that it is meant otherwise.

References to the Luminescent Oxygen Channeling Immunoassay (LOCI) methods and optical systems are for example only, and the inventive concepts can be used with any sample analysis procedure utilizing luminescence detection. Reference to a "sample" or "assay sample" refers to the sample to be analyzed and includes reagents added according to the analysis procedure, those reagents added either before or after insertion into the assay sample vessel.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Techniques utilizing chemiluminesence have been used to detect a great variety of analytes and samples in applications ranging from drug analysis to soil analysis and food chemistry. Liquid phase chemiluminescent analyses include enzyme assays and assays for carbohydrates, nucleotides, steroids and various drugs. As discussed in U.S. Pat. No. 7,402,281, various types of analytical tests related to patient diagnosis and therapy can be performed by analysis of a liquid sample taken from a patient's infections, bodily fluids or abscesses. Examples of bodily fluids include urine, whole blood, blood serum, blood plasma, saliva, cerebrospinal fluid, nasopharyngeal swab, vaginal swabs, sperm, tears, tissues (cellular materials) and the like.

An "immunoassay" measures the presence or concentration of an analyte, such as a hormone or enzyme, based on its ability to act as an antigen or antibody in a binding and chemical reaction. Chemiluminescent immunosassays utilize a chemiluminescent label that produces light when excited by chemical energy, usually coming from an oxidation-reduction reaction. The chemiluminescent molecules can be conjugated directly to antigens, or they can be used as substrates for enzyme labels. Commonly used chemiluminescent labels include acridinium esters, luminols, and dioxetanes.

A LOCI technique can be used to assay very small samples of plasma and is based on the proximity of two different coated synthetic particles or beads, a sensitizer bead (sensi-bead) containing a photosensitizer, and a chemiluminescer bead (chemi-bead) containing a chemiluminescer. In one LOCI procedure, streptavidin is bound to the surface of the sensitizer bead, which contains phthalcyanine that absorbs light at 680 nm to generate singlet oxygen. This allows use of commercially available 680 nm solid state laser or diodes for excitation. The chemiluminescer bead is coated with an analyte-specific antibody. Analyte in the sample binds to the analyte-specific antibody on a chemiluminescer bead and also binds to a biotinylated receptor reagent. The photosensitizer bead with streptavidin binds to the biotinylated receptor reagent: analyte: analyte-specific antibody:chemiluminescer complex thus causing formation of a particle dimer, i.e., the sensitizer bead linked with the chemiluminescer bead. The chemiluminescer bead contains an olefin dye (thioxene) which reacts with singlet oxygen, releasing light (chemiluminescence) at 390 nm. The short half life of the singlet oxygen ensures that the sensitizer bead must be in very close contact with the chemiluminescer bead to generate the chemiluminescence. Thus, creation of a particle dimer allows generation a chemiluminescent signal, while unassociated particles cannot generate chemiluminescent signals. A fluorescent energy acceptor (Europium Chelate) immediately shifts the emission wavelength to 612 nm, and the resulting light emission directly correlates with the amount of particle pairs or dimers, allowing quantification of the concentration of analyte in the sample.

Referring now to the drawings, and more particularly to FIG. 1, shown therein is an exemplary embodiment of a sample analyzer 10 constructed in accordance with the inventive concepts disclosed and claimed herein. The sample analyzer 10 comprises an illuminator 12 for illuminating an assay sample 14 to cause luminescence. A support 16 positions a sample vessel 18 containing the assay sample 14 such that the assay sample 14 is positioned proximate the illuminator 12. A reflector 20 is removably disposed between the illuminator 12 and the positioned assay sample 14. A detector 22 for detecting the luminescence is positioned along an optical axis 24 extending from the illuminator 12, through the positioned assay sample 14, to the detector 22. The sample analyzer 10 optionally includes a shutter 26 and a filter 28. The shutter 26 is used to protect high sensitivity detectors such as photomultiplier tubes (PMTs) from the illuminator 12 during an illumination phase of the assy. The filter 28 can be used to filter specific wave lengths of light to the detector 22.

As discussed in more detail hereinafter, the basic sample analysis process includes insertion of a liquid to be assayed into an assay sample vessel; irradiation (sometimes referred to hereinafter as "illumination") of the assay sample to cause the sample to luminesce; detection of the light emitted by the sample as a result of the irradiation or illumination; and correlation of the amount of detected light to the assay. Various types and configurations of assay sample vessels 18 can be used. In one embodiment, the assay sample vessel 18 is a microfluidic "card" having a disk-shaped sample reservoir 30. Such microfluidic cards are known to those skilled in the art.

Figure 2:
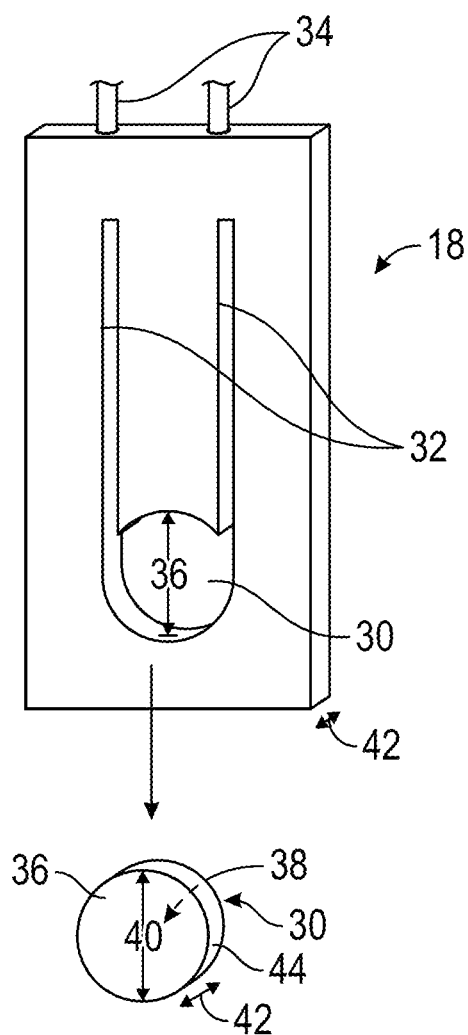
FIG. 2 is a schematic representation of an embodiment of a microfluidic card sample vessel constructed in accordance with the inventive concepts disclosed herein.

A simplified model of a microfluidic card is shown in FIG. 2. The model in FIG. 2 includes only the sample reservoir 30, fluid feeds 32 and fluid inlets 34. The sample reservoir 30 is shown as a circular or disc shaped feature toward the bottom of the card. An assay sample 14 can be delivered to the sample reservoir 30 through fluid feeds 32 by injecting the assay sample into one of the fluid inlets 34. The illuminating side 36 of sample reservoir 30, as well as the measuring side 38 of sample reservoir 30, is transparent to light from the illuminator 12 and to luminescent light from the assay sample. Such sample vessel design allows for a relatively thin sample reservoir 30 having a large diameter 40 relative to the thickness 42 of the sample reservoir 30. The thin sample reservoir provides a large surface area for the illuminating and measuring faces 36 and 38, respectively, relative to the surface area of an edge 44.

In one embodiment, the assay sample 14 is contained in a microfluidic card from about 50 mm to about 120 mm long, from about 30 mm to about 75 mm wide, and from about 2 mm to about 3 mm thick. The embedded circular or disc shaped sample reservoir 30 has a diameter of about 7 mm to 10 mm and an inside thickness of 1.5 mm to 2.5 mm. This provides a sample volume of about 50 to 200 µL. In another embodiment, the sample reservoir volume is less than 50 µL. While the size of the card can vary widely, and the shape of sample reservoir 30 is not limited to a circular disc, a thin sample reservoir providing a large surface area for the measuring face 38 relative to the surface area of the edge 44 decreases the luminescence lost through the edge 44, and thereby increases the light intensity reaching the detector. The thin sample reservoir also helps shorten the optical path length between the radiating assay sample 14 and the detector 22, thereby increasing the light intensity reaching the detector. In one embodiment, the intake optics of the detector 22 are positioned about 2 mm to 15 mm from the measuring side 38 of sample reservoir 30. In another embodiment, the intake optics 46 of the detector 22 are positioned about 2 mm to 7 mm from the measuring side 38 of sample reservoir 30.

Figure 3A:
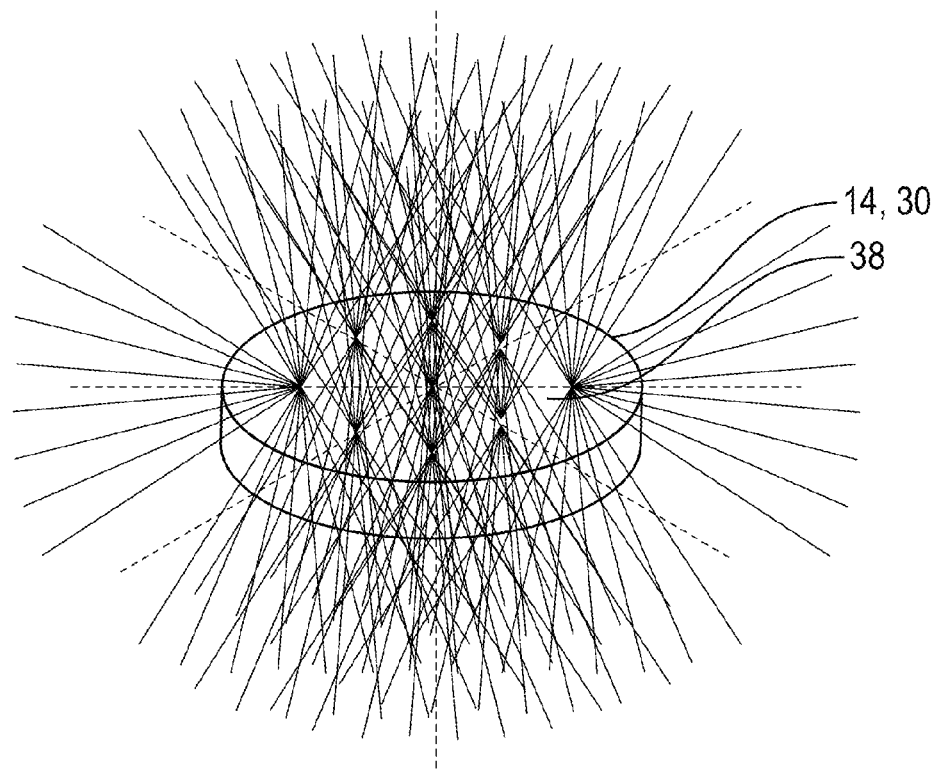
FIG. 3A is a model of light emitted by a luminescent sample in a disc shaped sample reservoir.

FIG. 3A shows modeling results of photon emission from a luminescent assay sample within a disc shaped sample reservoir 30. The photon emission pattern from the assay sample in the sample reservoir 30 is isotropic. Some photons emerge towards the detector 22 and some emerge away from it. As a consequence, emerging photons not incident to detector intake optics can be lost by scatter and absorption effects in the surrounding infrastructure, resulting in reaction relevant photons not being counted.

Figure 3B:
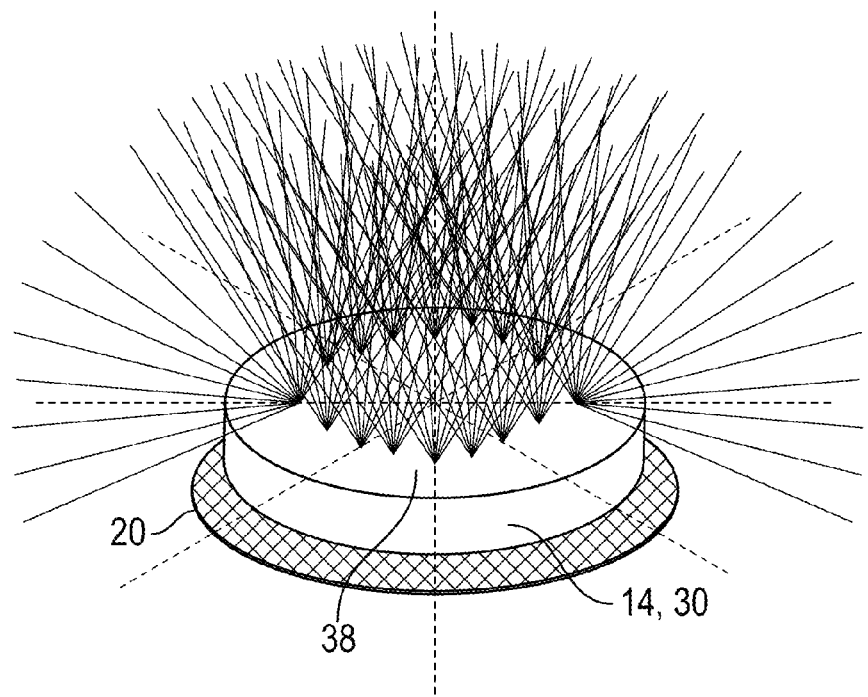
FIG. 3B is a model of light emitted by a luminescent sample in a disc shaped sample reservoir having a reflector adjacent one side.

FIG. 3B shows modeling results of photon emission from a luminescent assay sample within a disc shaped sample reservoir 30 having a reflector 20 adjacent one face of the sample reservoir 30. Photons that emerge from the assay sample in a direction away from the detector 22 are now reflected off the reflector 20, back through the assay sample 14, and out the measuring face 38 of the sample reservoir 30. More of the photons are directed toward the detector 22, and measurement of photon emission is significantly improved.

The detector 22 can be any photo-detector having a sensitivity required by the particular assay. Vacuum photodetectors such as photomultiplier tubes (PMTs) are typically very sensitive. Solid state photodetectors such as silicon photodiodes are often used when less sensitivity is required. Such detectors and their use are well known to those skilled in the art. The detector 22, using photon-counting electronics, measures light emission from the assay sample 14 over a defined time interval, typically around 10 seconds. The analyte concentration in the assay sample 14 is directly proportional to the assay sample volume and the photon production. Sample analyzer software computes the analyte concentration from the photon count. During manufacture, the sample analyzer 10 can be calibrated using a set of standards of known analyte concentration to insure accurate assay reporting.

Figure 4C:
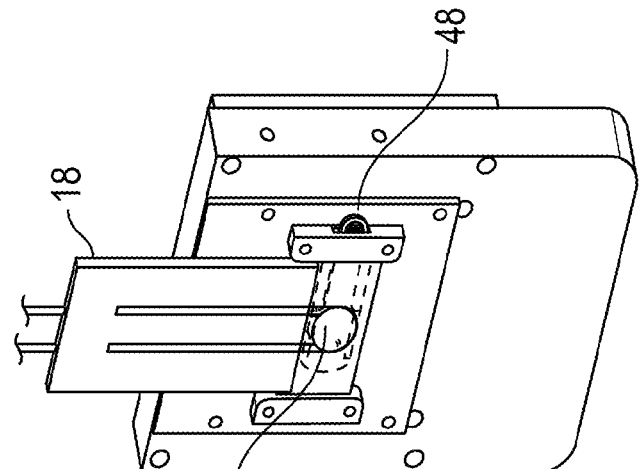
FIG. 4C is yet another view of the embodiment shown in FIG. 4A, illustrating the assay vessel 30 in alignment with the optical axis 24.
Figure 4B:
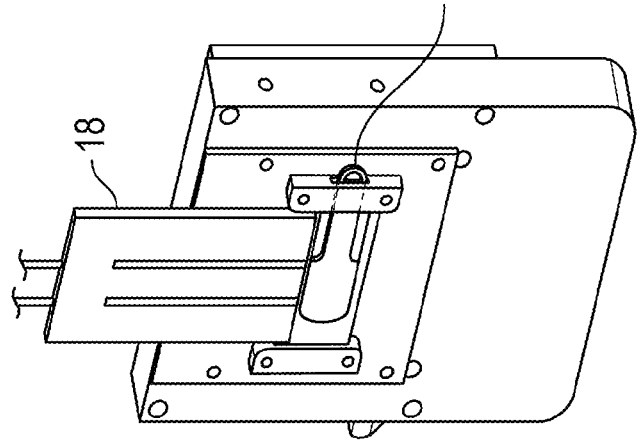
FIG. 4B is another view of the embodiment shown in FIG. 4A, illustrating the reflector 48.
Figure 4A:
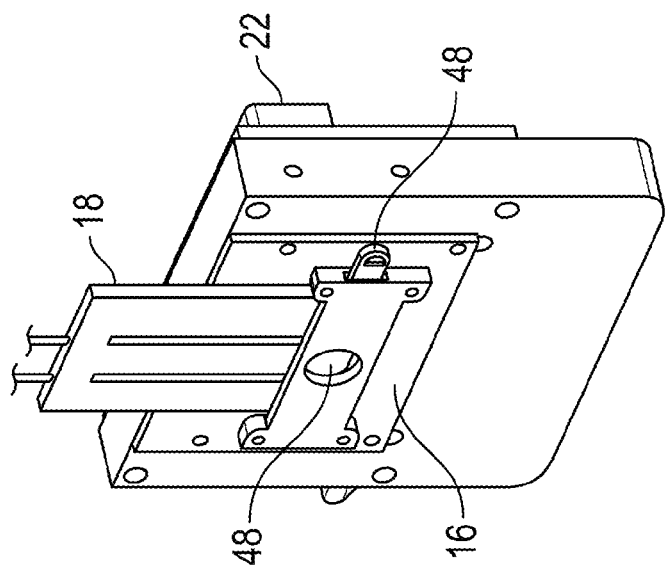
FIG. 4A is a schematic representation of an embodiment of a sample analyzer having a reflector and shuttle constructed in accordance with the inventive concepts disclosed herein.

In one embodiment, the sample analyzer 10 is configured to provide back illumination and front detection relative to the assay sample positioned in between. Thus, the reflector 20 is moved out of position during the catalyzing illumination portion of the analysis, and into position adjacent the illuminating face 36 of the sample reservoir 30 during the detection portion of the analysis. As illustrated in FIG. 4A though FIG. 4C, the reflector 20 is positioned on a shuttle 48 which, by means of a shuttle actuator mechanism (not shown), is "shuttled" out of the way of the illumination path during the illumination interval when light shines into the assay sample reservoir 30 to start the reaction and photon emission. After the illumination interval, the assay sample 14 begins to respond by emitting photons, and the reflector 20 is shuttled into position behind the assay sample reservoir, thereby reflecting photons towards the detector 22. Nonlimiting examples of a suitable shuttle actuator mechanism include a battery operated solenoid with linkage to the shuttle working against a spring, a rotary torque motor doing a swipe, an electric motor with a rack-and-pinion gear set connected to the shuttle, a stepper motor meshed with the shuttle, and the like. In one embodiment, the shuttle actuation is integrated with the actuation of the shutter 26.

The image in FIG. 4A shows the reflector 20 in a reflect position, and a portion of the support 16 used to also support the shuttle 48 in a slideable fashion. The image in FIG. 4B shows more of the shuttle 48 with the reflector 20 still in a reflect position. The image FIG. 4C shows the reflector 20 and the shuttle 48 as translucent so that a silhouette of the sample reservoir 30 can be seen.

The reflector 20 can be flat or curved and can include any material having suitable reflective properties. Two example reflectors tested were a commercially available 1 mm thick flat mirror and a custom parabolic spline reflector. The parabolic reflector can be manufactured using a vacuum deposition process over a plastic form. Tests with the flat mirror reflector showed a measured improvement in signal gain of 1.5 times compared to the measurement without the reflector. Tests with the parabolic reflector showed a signal gain of 2 times that obtained without the reflector.

During the illumination interval, when light shines into the assay sample reservoir 30 to start the reaction and photon emission, the reflector 20 is held out of the way by the shuttle 48 and shuttle actuator mechanism so that the illumination can strike the illuminating face 36 of the sample reservoir 30 unobstructed. Light intensity and time of irradiation may vary widely. The illuminator 12 can be multi-wavelength, optionally filtered to cut off undesired wavelengths, or can be a laser providing monochromatic light. In one embodiment, light emitting diodes (LEDs) are used. In another embodiment, the illuminator 12 comprises multiple LEDs arranged in a ring or an array of closely spaced LED die.

In yet another embodiment, a diffuser 50 is disposed between the illuminator 12 and the shuttle 48. With the diffuser 50 so positioned, and the reflector 20 held out of the way, the illuminating light must pass through the diffuser 50 before contacting the assay sample 14 in the sample reservoir 30. Diffuser 50 helps provide more uniform illumination and more uniform flux density across the assay sample, without incurring additional optical path distance. By not incurring additional distance between the illuminator 12 and the sample reservoir 30, less power input is required to achieve the same assay activation behavior. The diffuser allows the illuminator to be positioned less than 10 mm from the positioned assay sample, and in one embodiment less that 3 mm from the positioned assay sample, while still providing uniform illumination. This helps to provide a significant decrease in the overall size of the sample analyzer 10.

Figure 5A:
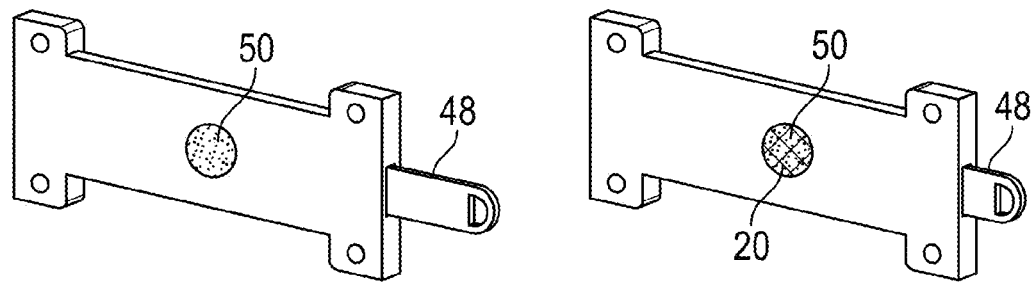
FIG. 5A depicts the shuttle in FIG. 4 viewed from the illuminator side.
Figure 5B:
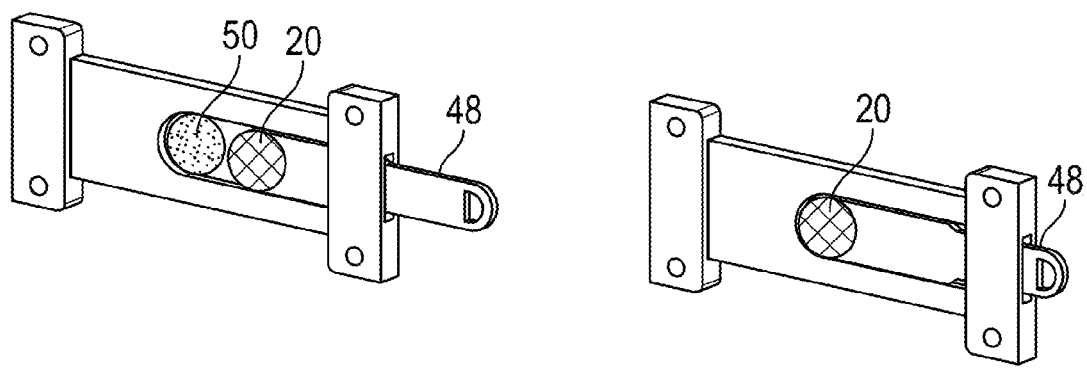
FIG. 5B depicts the shuttle in FIG. 4 viewed from the sample vessel side.

After the illumination interval is complete, the reflector 20 is moved or "shuttled" into position behind the assay sample reservoir 30. After the reflector 20 settles, the detector shutter 26 is opened presenting the assay sample photon emission to the detector intake optics 46. FIG. 5A depicts the shuttle viewed from the illuminator side. The left image shows the reflector shuttled out of the way of the illumination path and the diffuser 50 exposed for an illumination interval. In this embodiment, the diffuser 50 position is fixed in optical alignment between the illuminator 12 and the sample reservoir 30. The right image shows the reflector 20 positioned to reflect photons emitted from the assay sample in a measuring interval, covering the otherwise exposed diffuser 50. FIG. 5B depicts the shuttle viewed from the assay sample side. The left image shows the reflector shuttled out of the way of the illumination path leaving the diffuser 50 exposed for an illumination interval. The right image shows the reflector 20 positioned by the shuttle to reflect photons emitted from the assay sample during a measuring interval.

In another embodiment of the presently disclosed inventive concept(s), the position of the diffuser 50 is not fixed. Instead, both the reflector 20 and the diffuser 50 are present on the shuttle 48 such that their positions are controlled by the shuttle 48 to align as described above.

In the following examples, specific assays are described. However, the present inventive concept(s) is not be limited in its application to the specific experimentation, results and laboratory procedures. Rather, the Examples are simply provided as one of various embodiments and are meant to be exemplary, not exhaustive.

EXAMPLES

Figure 6:
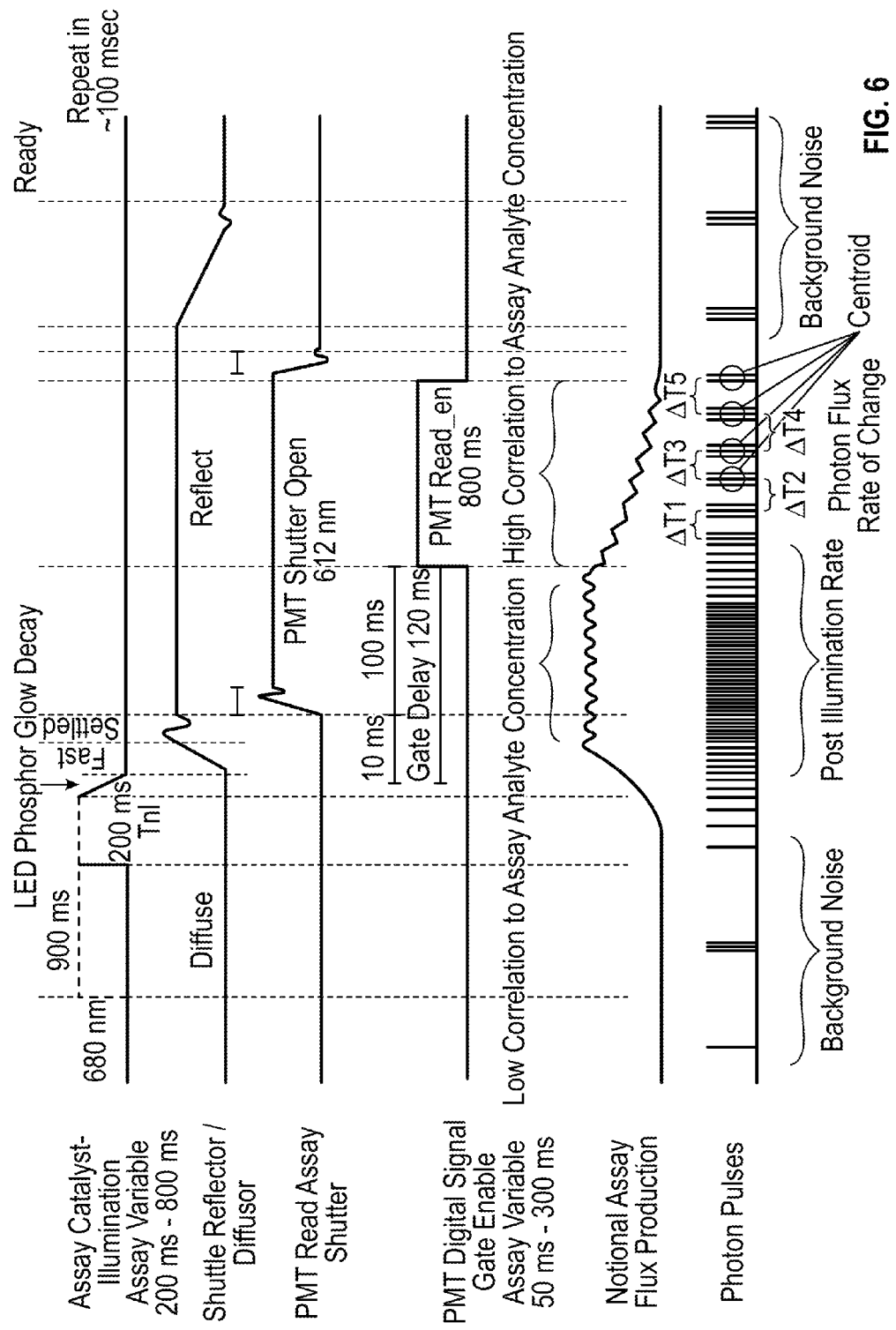
FIG. 6 is a timing diagram for an embodiment of a sample analyzer operation in accordance with the inventive concepts disclosed herein.

In a typical assay method such as for Troponin I, a patient blood plasma sample is mixed with chemi-bead reagents and incubated incubated. Sensi-bead reagents are added and the resulting assay sample is illuminated with 680 nm light. This causes singlet oxygen generation and shortly afterward emission of 612 nm photons which are measured by an optical detection system. FIG. 6 is an example timing diagram depicting a LOCI Troponin I assay. Process timing is shown for the illumination step, shuttle operation for diffuser or reflector modes, operation of photomultiplier shutter and signal gates, and the production and analysis of photons emitted from the catalyst in the assay sample.

The LOCI Troponin I assay was performed using a prototype portable, battery operated, sample analyzer operated with a reflector and without a reflector. The assay sample was contained in a microfluidic module "card" about 80 mm long×50 mm wide×2.5 mm thick, having an embedded circular assay sample reservoir. The inner surface of the reservoir was 8.5 mm in diameter and 2 mm in depth. The 8.5 mm diameter cylinder faced normal to the detector optics centerline. The intake optics of the detector were 5 mm from the measuring side of the sample reservoir. A 680 nm catalyzing illumination LED array ring was 2.55 mm from the illuminating side (opposite the measuring side) of the sample reservoir.

Figure 7:
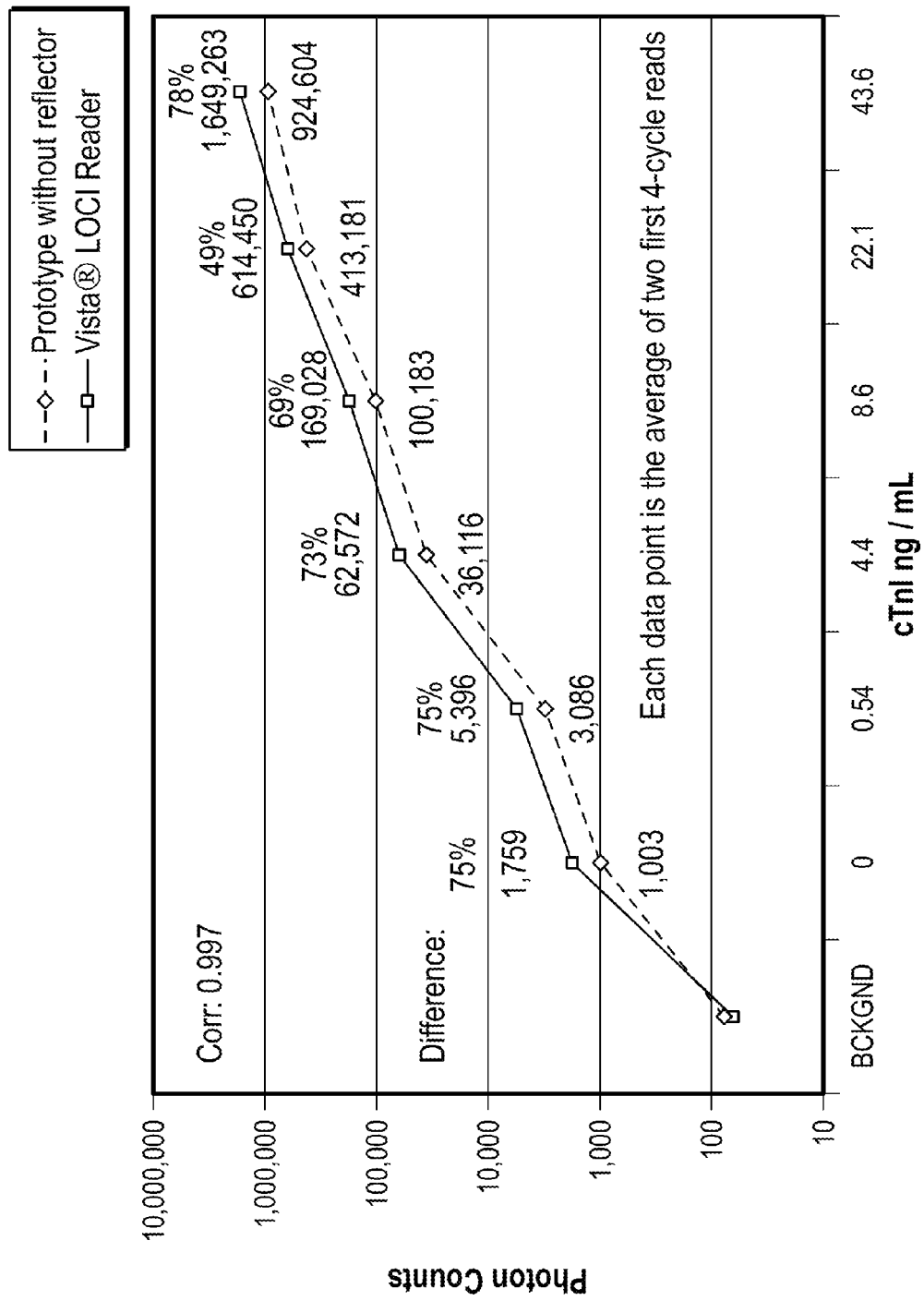
FIG. 7 is a graph of photon counts from a prototype reader depicting good correlation to a commercial VISTA® LOCI Reader.

To evaluate the performance of the reflector, measurements were initially taken without the reflector in place and compared to measurements using a commercial VISTA® LOCI Reader. The VISTA® LOCI Reader has a considerably different geometry compared to the prototype. In the VISTA® LOCI reader, the sample illumination LEDs, are positioned at the left and right sides of the assay vessel relative to the detector center line. Photon counts were made for a wide range of Troponin I assay dilutions. Results for the prototype without a reflector are compared to those of the commercial VISTA® LOCI Reader in FIG. 7. As can be seen, the response correlation was excellent; however, the actual photon counts were significantly lower for the prototype without a reflector.

Figure 8:
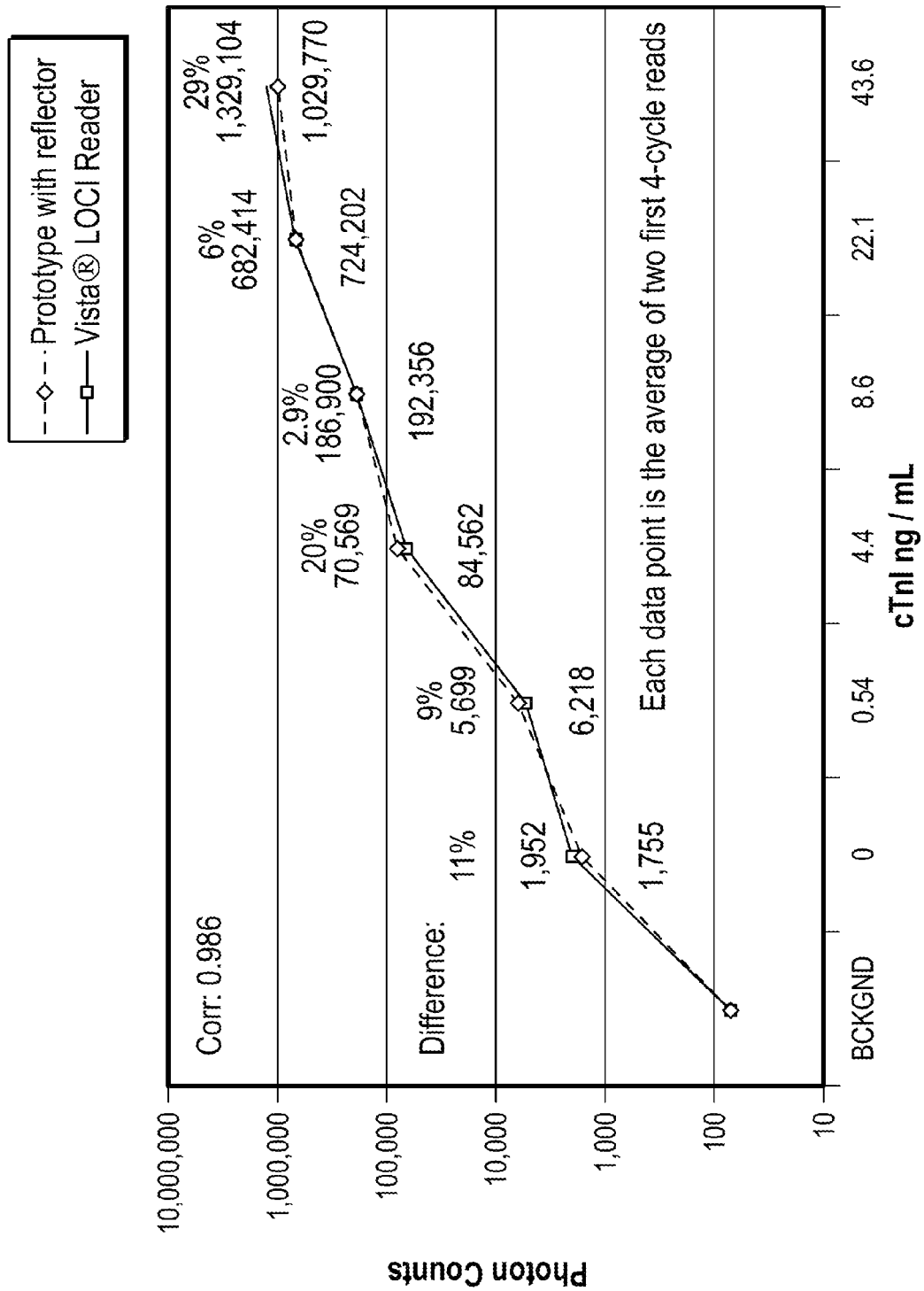
FIG. 8 is a graph of photon counts from a prototype reader according to one embodiment of the present invention demonstrating improved performance with a reflector and compared to a commercial VISTA® LOCI Reader.

The response signals improved about 60% when the reflector was enabled. FIG. 8 shows Troponin I assay results using the above-described prototype with a reflector, and compared to results from the VISTA® LOCI Reader. Differences in photon counts are quite small.

From the above description, it is clear that the inventive concept(s) disclosed herein is well adapted to carry out the objectives and to attain the advantages mentioned herein as well as those inherent in the inventive concept disclosed herein. While exemplary embodiments of the inventive concept disclosed herein have been described for purposes of this disclosure, it will be understood that numerous changes may be made which will readily suggest themselves to those skilled in the art and which are accomplished without departing from the scope of the inventive concept disclosed herein and defined by the appended claims.

What is claimed is:

1. A sample analyzer, comprising:
an illuminator;
a support positioned to support a sample vessel containing an assay sample proximate the illuminator;
a detector positioned along an optical axis extending from the illuminator, through the assay sample, to the detector, so as to detect luminescence of the assay sample;
a shuttle disposed between the illuminator and the assay sample, the shuttle being moveable perpendicular with the optical axis; and
a reflector disposed on the shuttle,
wherein the apparatus is configured with an illumination mode and a measurement mode,
wherein during the illumination mode the shuttle positions the reflector off the optical axis,
and the illuminator is operated to illuminate the assay sample,
wherein during the measurement mode the illuminator is operated to discontinue illuminating the sample,
further wherein during the measurement mode the shuttle positions the reflector onto the optical axis such that residual light traveling along the optical axis from the discontinued illuminator is shut off from the assay sample and luminescence from the assay sample is reflected off the reflector back through the assay sample towards the detector along the optical axis.

2. The sample analyzer of claim 1, wherein the detector is positioned from about 2 mm to about 15 mm from the assay sample.

3. The sample analyzer of claim 1, wherein the detector is positioned from about 2 mm to about 7 mm from the assay sample.

4. The sample analyzer of claim 1, wherein the detector comprises a photomultiplier tube, or a high sensitivity silicon avalanche photodiode detector.

5. The sample analyzer of claim 1, wherein the reflector is a flat mirror.

6. The sample analyzer of claim 1, wherein the reflector is a parabolic conic reflector.

7. The sample analyzer of claim 1, wherein the illuminator is positioned less than 10 mm from the assay sample.

8. The sample analyzer of claim 1, wherein the assay sample is contained in a disc shaped sample reservoir in the sample vessel.

9. The sample analyzer of claim 8, wherein the disc shaped sample reservoir has an inside thickness of from about 1.5 mm to about 2.5 mm.

10. A method of analyzing an assay sample, comprising:
obtaining a sample analyzer comprising:
an illuminator;
a support positioned to support a sample vessel containing an assay sample proximate the illuminator;
a detector positioned along an optical axis extending from the illuminator, through the assay sample, to the detector so as to detect luminescence of the assay sample;
a shuttle disposed between the illuminator and the assay sample, the shuttle being moveable perpendicular to the optical axis; and
a reflector disposed on the shuttle;
supporting the sample vessel containing the assay sample proximate to the illuminator;
illuminating the assay sample to cause luminescence of the assay sample during an illumination mode of the sample analyzer;
and
measuring the luminescence of the assay
sample during a measurement mode of the sample analyzer,
wherein during the illumination mode the shuttle positions the reflector off the optical axis
and the illuminator is operated to illuminate the assay sample,
wherein during the measurement mode the illuminator is operated to discontinue illuminating the sample,
further wherein during the measurement mode the shuttle positions the reflector onto the optical axis such that residual light traveling along the optical axis from the discontinued illuminator is shut off from the assay sample and luminescence from the assay sample is reflected off the reflector back through the assay sample towards the detector along the optical axis.

11. The method of claim 10, wherein an analyte concentration in the assay
sample is determined by measuring the luminescence at and for predetermined times and, using
sample analyzer software, calculating the analyte concentration in the assay sample from the
measured luminescence.

12. The method of claim 10, wherein the assay sample is contained in a disc shaped sample reservoir in the sample vessel.

13. The method of claim 12, wherein the disc shaped sample reservoir has an inside thickness of from about 1.5 mm to about 2.5 mm.

14. The method of claim 10, wherein the detector is positioned from about 3 mm to about 7 mm from the assay sample.

15. The method of claim 10, wherein the detector is a photomultiplier tube.

16. The method of claim 10, wherein the reflector is a flat mirror.

17. The method of claim 10, wherein the reflector is a parabolic conic reflector.

18. The method of claim 10, wherein the illuminator is positioned less than 10 mm from the assay sample.

19. The sample analyzer of claim 1, further comprising:
a light diffuser disposed on the shuttle, wherein during the illumination mode the shuttle
positions the diffuser onto the optical axis
such that light traveling along the optical axis from the illuminator towards the assay sample passes through the diffuser.

20. The sample analyzer of claim 19, wherein during the measurement mode the shuttle positions the light diffuser off the optical axis.

21. The method of claim 10, wherein the sample analyzer further
comprises a light diffuser disposed on the shuttle, wherein during the illumination mode the shuttle
positions the diffuser onto the optical axis such that light traveling along the optical axis from the illuminator towards the assay sample passes through the diffuser.

22. The method of claim 21, wherein during the measurement mode the shuttle positions the light diffuser.

* * * * *